(12) United States Patent
Dotan et al.

(10) Patent No.: US 9,119,539 B1
(45) Date of Patent: *Sep. 1, 2015

(54) PERFORMING AN AUTHENTICATION OPERATION DURING USER ACCESS TO A COMPUTERIZED RESOURCE

(75) Inventors: Yedidya Dotan, Tel Aviv (IS); Lawrence N. Friedman, Arlington, MA (US); William M. Duane, Westford, MA (US)

(73) Assignee: EMC Corporation, Hopkinton, MA (US)

( * ) Notice: Subject to any disclaimer, the term of this patent is extended or adjusted under 35 U.S.C. 154(b) by 228 days.

This patent is subject to a terminal disclaimer.

(21) Appl. No.: 13/432,732

(22) Filed: Mar. 28, 2012

Related U.S. Application Data

(63) Continuation-in-part of application No. 13/336,573, filed on Dec. 23, 2011, now Pat. No. 8,902,045.

(51) Int. Cl.
*G08B 21/00* (2006.01)
*A61B 5/024* (2006.01)

(52) U.S. Cl.
CPC .................................. *A61B 5/02438* (2013.01)

(58) Field of Classification Search
CPC .................. A61B 5/02416; A61B 2560/0462; A61B 5/02438; A61B 5/0255; A61B 5/22
USPC ............ 340/5.52, 5.53, 5.8, 5.81, 5.82, 5.83; 382/115, 173; 707/100
See application file for complete search history.

(56) References Cited

U.S. PATENT DOCUMENTS

| | | | |
|---|---|---|---|
| 2002/0149467 A1* | 10/2002 | Calvesio et al. | 340/5.52 |
| 2004/0133547 A1* | 7/2004 | Doi | 707/1 |
| 2007/0009139 A1* | 1/2007 | Landschaft et al. | 382/115 |
| 2007/0024422 A1* | 2/2007 | Doyen | 340/5.81 |
| 2009/0134972 A1* | 5/2009 | Wu et al. | 340/5.82 |
| 2009/0312647 A1* | 12/2009 | Kasama | 600/483 |

* cited by examiner

*Primary Examiner* — Mark Rushing
(74) *Attorney, Agent, or Firm* — Krishnendu Gupta; Jason A. Reyes

(57) ABSTRACT

A method, electronic apparatus and computer program product for performing authentication operation is disclosed. An authentication request is received from user of computerized resource. The request comprises user identifier identifying user. The authenticity of user is verified based on user identifier. An access session is established in which user can access resource in response to successfully verifying user. An electronic input signal is received from electronic input device during session. The device is configured to take a biometric measurement from the user. Biometric data is derived from signal. A comparison is performed between biometric data and expected biometric data. An authentication result is generated based on comparison between biometric data and expected biometric data, wherein result can be used for further authentication of user during session.

17 Claims, 7 Drawing Sheets

PERFORMING AN AUTHENTICATION OPERATION DURING USER ACCESS TO A COMPUTERIZED RESOURCE

RELATED APPLICATION

This application is a continuation-in-part application claiming priority to co-pending U.S. patent application Ser. No. 13/336,573, filed Dec. 23, 2011, reference no. EMC-11-651, entitled "AUTHENTICATION USING PULSE DATA", the entirety of which patent application is hereby incorporated by reference herein.

TECHNICAL FIELD

The present invention relates to performing an authentication operation.

BACKGROUND OF THE INVENTION

Generally, security systems employ an identity-based authentication scheme to verify the identity of an entity before granting access to a computer system or a computerized resource. One goal of such security systems is to accurately determine identity so that an unauthorized party cannot gain access. Security systems can use one or more of several factors, alone or in combination, to authenticate entities. For example, identification systems can be based on something that the entity knows, something the entity is, or something that the entity has.

Examples of something an entity knows are a code word, password, personal identification number ("PIN") and the like. One exemplary computer-based authentication method involves the communication of a secret that is specific to a particular entity or user. The entity seeking authentication transmits the secret or a value derived from the secret to a verifier, which authenticates the identity of the entity. In a typical implementation, an entity communicates both identifying information (e.g., a user name) and a secret (e.g., a password) to the verifier. The verifier typically possesses records that associate a secret with each entity. If the verifier receives the appropriate secret for the entity, the entity is successfully authenticated. If the verifier does not receive the correct secret, the authentication fails.

Examples of something the entity is include a distinct characteristic or attribute known as a biometric. It will be known by those skilled in the art that a biometric is a unique physical or behavioral characteristic or attribute that can be used to identify a person uniquely. Biometrics encompass a variety of techniques designed to accurately identify a person including fingerprinting, facial recognition, retina blood vessel patterns, DNA sequences, voice and body movement recognition, handwriting and signature recognition. Examples of advances in biometric technology include devices such as a biometric mouse that can offer a fingerprint reader and the capacity for collection of specific user clickstream data for statistical analysis. It will appreciated that suitable physical or behavioral characteristics or attributes are typically not under the control of the person, and are therefore difficult for anyone besides the intended person to present, because, in part, they are difficult to replicate. The verifier typically can observe these physical or behavioral characteristics or attributes and compare these to records that associate the characteristics or attributes with the entity. The observation of these characteristics or attributes is referred to generally as biometric measurement.

An example of something an entity possesses is a physical or digital object, referred to generally as a token, that is unique, or relatively unique, to the user. It will be appreciated that possession of a token such as a bank card having certain specific physical and electronic characteristics, for example containing a specific identification number that is revealed when the token is accessed in a particular manner, can be this type of factor. A token containing a computing device that performs encryption using an encryption key contained in the device would also be regarded as this type of factor. For example, a token could accept user input, which might include a PIN or a challenge value, and provide as output a result encrypted with a secret encryption key stored in the card. The verifier can then compare the output to an expected value in order to authenticate the entity.

However, if an entity is successful in authenticating their identity by virtue of what the entity knows, something the entity is, or something that the entity has, the security access to the computer system or computerized resource may be granted for an unlimited time period. This is undesirable.

SUMMARY OF THE INVENTION

A method, electronic apparatus and computer program product for performing an authentication operation is disclosed. An authentication request is received from a user of a computerized resource. The request comprises a user identifier identifying the user. The authenticity of the user is verified based on the user identifier identifying the user. An access session is established in which the user can access the computerized resource in response to successfully verifying the authenticity of the user. An electronic input signal is received from an electronic input device during the access session. The electronic input device is configured to take a biometric measurement from the user. Biometric data is derived from the electronic input signal. A comparison is performed between the biometric data from the user and expected biometric data for the user. An authentication result is generated based on the comparison between the biometric data and the expected biometric data, wherein the authentication result can be used for further authentication of the user during the access session.

BRIEF DESCRIPTION OF THE DRAWINGS

Features and advantages of the present invention will become more apparent from the following detailed description of exemplary embodiments thereof taken in conjunction with the accompanying drawings in which.

DETAILED DESCRIPTION

The invention can be implemented in numerous ways, including as a process, an apparatus, a system, a computer program embodied on a computer readable storage medium, and/or a processor, such as a processor configured to execute instructions stored on and/or provided by a memory coupled to the processor. In this specification, the implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Figure 1:
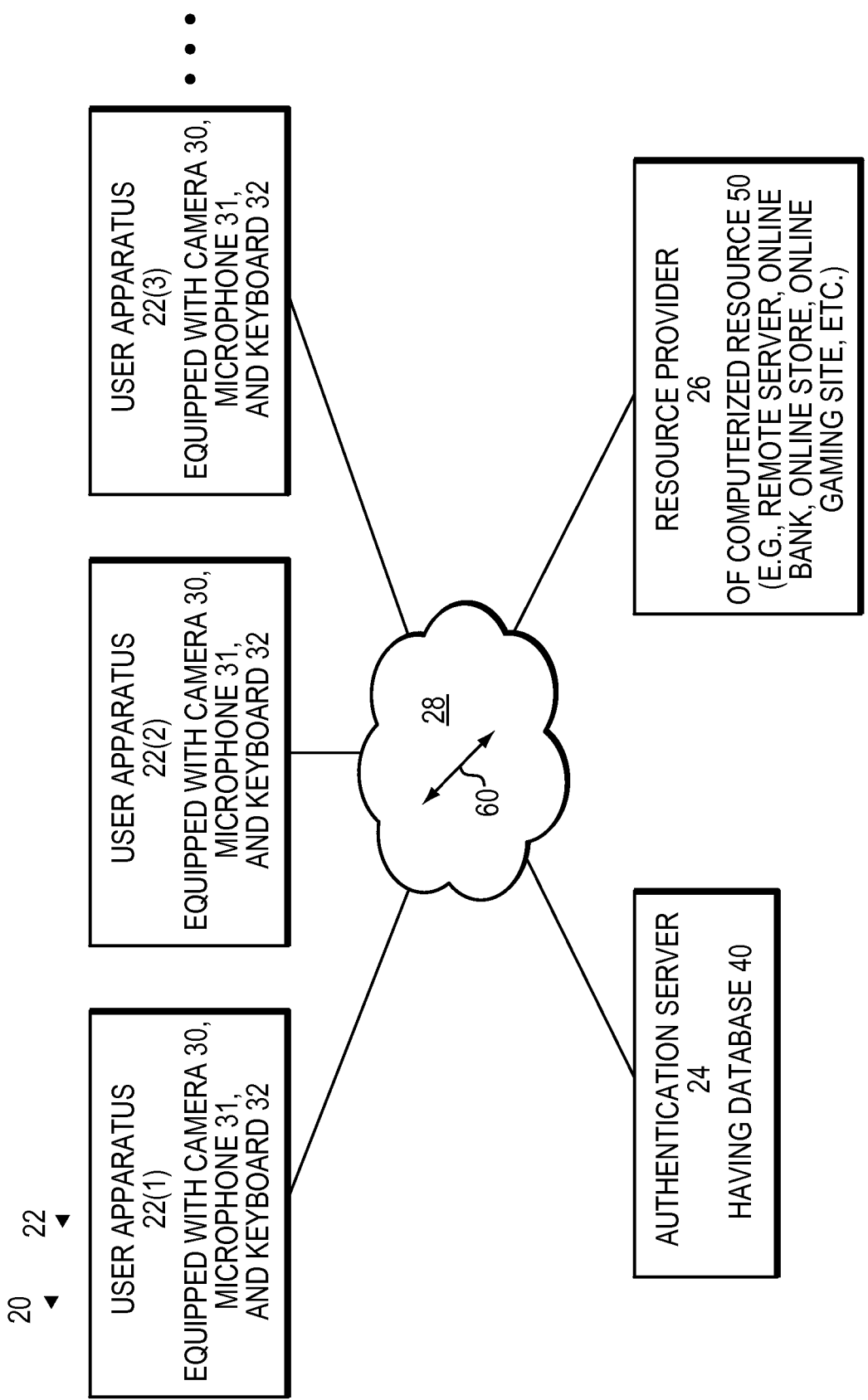
FIG. 1 is a block diagram of an example environment for performing authentication operations.

Referring to FIG. 1, there is illustrated an example of an environment 20 which performs authentication operations. The environment 20 includes user apparatus 22(1), 22(2), 22(3), ... (collectively, user apparatus 22), an authentication server 24, a resource provider 26, and communications medium 28.

Each user apparatus 22 is equipped with a camera 30. With their respective cameras 30, each user apparatus 22 has the ability to capture video. For example, the user apparatus 22(1) may be a general purpose computer with a webcam. Similarly, the user apparatus 22(2) may be a tablet with a built-in digital camera. Additionally, the user apparatus 22(3) may be a smart phone with a built-in camera, and so on. With such cameras 30, the user apparatus 22 are suitable for capturing detailed moving color video input (i.e., sequences of video frames) of human faces suitable for use in authentication.

Additionally, each user apparatus 22 is also equipped with a microphone 31 and a keyboard 32. It will be appreciated that the keyboard 32 may be a button operated keyboard or a touch screen keyboard. For example, the general purpose computer 22(1) may comprise a camera, a microphone and a button operated keyboard. The tablet 22(2) and the smart phone 22(3) may comprise a camera, a microphone and a touch screen keyboard. It will be appreciated that in this embodiment the click rate of a user or a user input rhythm in connection with the keyboard 32 is suitable for use in authenticating a user. With the microphone 31, the user apparatus 22 is also suitable for capturing the sound of a human voice for use in authentication.

The authentication server 24 includes a database 40. The authentication server 24 is constructed and arranged to store biometric data in the database 40 and to perform authentication operations using the biometric data (e.g., biometric similarity evaluations). For example, the database 40 may include biometric data relating to fingerprints, facial features, retina blood vessel patterns, DNA sequences, voice and body movements, handwriting and signature. The database may also include clickstream data for statistical analysis. It will be known in the art that individuals have distinct click rates enabling the identity of an individual to be identified by clickstream analytics. The database 40 may contain such data enabling identification of the individual.

In this particular embodiment, the biometric data stored in the database 40 includes cardiac pulse waveform data from multiple users. In some arrangements, the cardiac pulse waveform data may include detailed representations of actual human pulse waveforms and a captured video of the users face (e.g., to accommodate future waveform matching techniques). In other arrangements, the cardiac pulse waveform data includes only waveform measurements of particular parts of the actual human pulse waveforms (e.g., to optimize back-end processing and minimize storage). In yet other arrangements, the cardiac pulse waveform data includes both detailed representations of actual human pulse waveforms as well as waveform measurements of particular parts of the actual human pulse waveforms (e.g., to provide greatest flexibility).

The resource provider 26 provides each user apparatus 22 with access to one or more computerized resources 50 following successful user authentication through the user apparatus 22. An example of a suitable resource provider 26 is a data storage array which provides secure access to files, directories, volumes, LUNs, etc. Another example of a suitable resource provider 26 is a web server which provides secure access to various web pages. Yet another example of a suitable resource provider 26 is a server which provides secure user account and/or transactional access such as that for an online banking site, an online store, an online gaming site, and so on. Other types of resource providers are suitable for use as well.

The communications medium 28 connects the various components of the environment 20 together to enable these components to exchange electronic signals 60 (e.g., see the double arrow 60). At least a portion of the communications medium 28 is illustrated as a cloud to indicate that the communications medium 28 is capable of having a variety of different topologies including backbone, hub-and-spoke, loop, irregular, combinations thereof, and so on. Along these lines, the communications medium 28 may include copper-based devices and cabling, fiber optic devices and cabling, wireless devices, combinations thereof, etc.

During operation, the authentication server 24 receives an authentication request comprising a user identifier from a user of computerized resource 50. It should be understood that an authentication request may involve submitting or transmitting a user identifier such as a username and/or password. Alternatively, the authentication request may involve submitting or transmitting biometric identification so that the submitted biometric identification acts as the user identifier. In such an arrangement, the biometric identification (e.g., based on the user's face) avoids the need to enter a username and/or password. It will be appreciated that the authentication server 24 may receive the authentication request directly from the user apparatus 22 (i.e., the user attempts to authenticate directly with the authentication server 24) or indirectly through the remote protected resource 26 (i.e., the user attempts to authenticate with the remote protected resource 26 which then delegates the authentication task to the authentication server 24). The processing circuitry of the environment 20 will receive the request and verify the user based on the user identifier. For example, the authentication request may involve the user apparatus capturing and submitting a video of the users face such that the users face acts as the user identifier facilitating identification of the user. The processing circuitry receives the request comprising the user identifier and queries the database 40 using the user identifier 150 in order to obtain biometric data stored in the database for that particular user. For example, the biometric data in the database 40 may comprise expected pulse data for the user. The processing circuitry may derive current pulse data from the video input of the users face and perform a comparison between the current pulse data and expected pulse data stored in the database in order to verify the user. The processing circuitry establishes an access session in which the user can access the computerized resource 50 in response to successful verification of the authenticity of the user.

In one embodiment, the authentication operation is repeated over the access session. In such continuous authentication, the user of the user apparatus 22 will have their face captured by the camera 30 of the user apparatus 22 during the access session. For example, the users face may be captured continuously during the access session by the camera for delivering a constant stream of biometric data that can be used to authenticate the user continuously throughout the access session. The processing circuitry will receive the current video input of the users face during the access session, obtain or derive current pulse data from the current video input, perform a comparison between the current pulse data and expected pulse data stored in the database 40 and generate an authentication result based on the comparison between the current pulse data and the expected pulse data. The authentication result is used for authenticating the user during the access session. It will be appreciated that the authentication result controls continuous user access to the computerized resource 50 during the access session.

In these arrangements, the authentication server 24 performs a set of blind source separation operations on the video input to identify or derive a current pulse waveform of the user from the video input. Those of skill in the art will appreciate that such blind source separation operations enable convenient separation of the current pulse waveform from other signals mixed within the video input. The authentication server 24 then retrieves an expected pulse waveform for the user from the database 40. The authentication server 24 then compares measurements of the current pulse waveform to measurements of the expected pulse waveform to determine whether the user is authentic or an imposter. Along these lines, it should be understood that each pulse waveform has particular parts which are recognizable and measurable (e.g., amplitude, timing, shape, etc. of the P wave, the T wave, and so on) in order to determine a level of similarity between such patterns. A detailed discussion of the distinctive aspects of a human electrocardiogram (ECG) is provided in a research paper entitled "Implementation of one-lead ECG human identification system on a normal population", written by Tsu-Wang (David) Shen, Willis J Tompkins and Yu Hen Hu, and provided by the Journal of Engineering and Computer Innovations Vol. 2(1), pp. 12-21, January, 2011, the contents and teachings of which are hereby incorporated by reference in their entirety (hereinafter referred to as "the Shen reference").

In some arrangements, the user apparatus 22 which captures the video input is further tasked with performing the set of blind source separation operations on the video input to identify the current pulse waveform of the user. In these arrangements, the user apparatus 22 then sends a computerized representation of the current pulse waveform of the user to the authentication server 24 which, in turn, completes the authentication process. Such offloading of the blind source separation operations from the authentication server 24 to the user apparatus 22 lowers bandwidth through the communications medium 28 and consumes less processing resources at the authentication server 24.

In other arrangements, each user apparatus 22 not only performs the set of blind source separation operations on the video input, but also locally stores a representation or measurements of the expected pulse waveform for the user as well as performs the comparison operation. In these arrangements, each user apparatus 22 essentially operates as its own localized authentication server 24 to perform the entire authentication process including the comparison of waveform measurements.

It should be understood that various other modifications can be made to create other arrangements. For instance, in some arrangements, the computerized resource 50 resides locally within the user apparatus 22. Additionally, the environment 20 is suitable to support various combinations of these arrangements.

Figure 2:
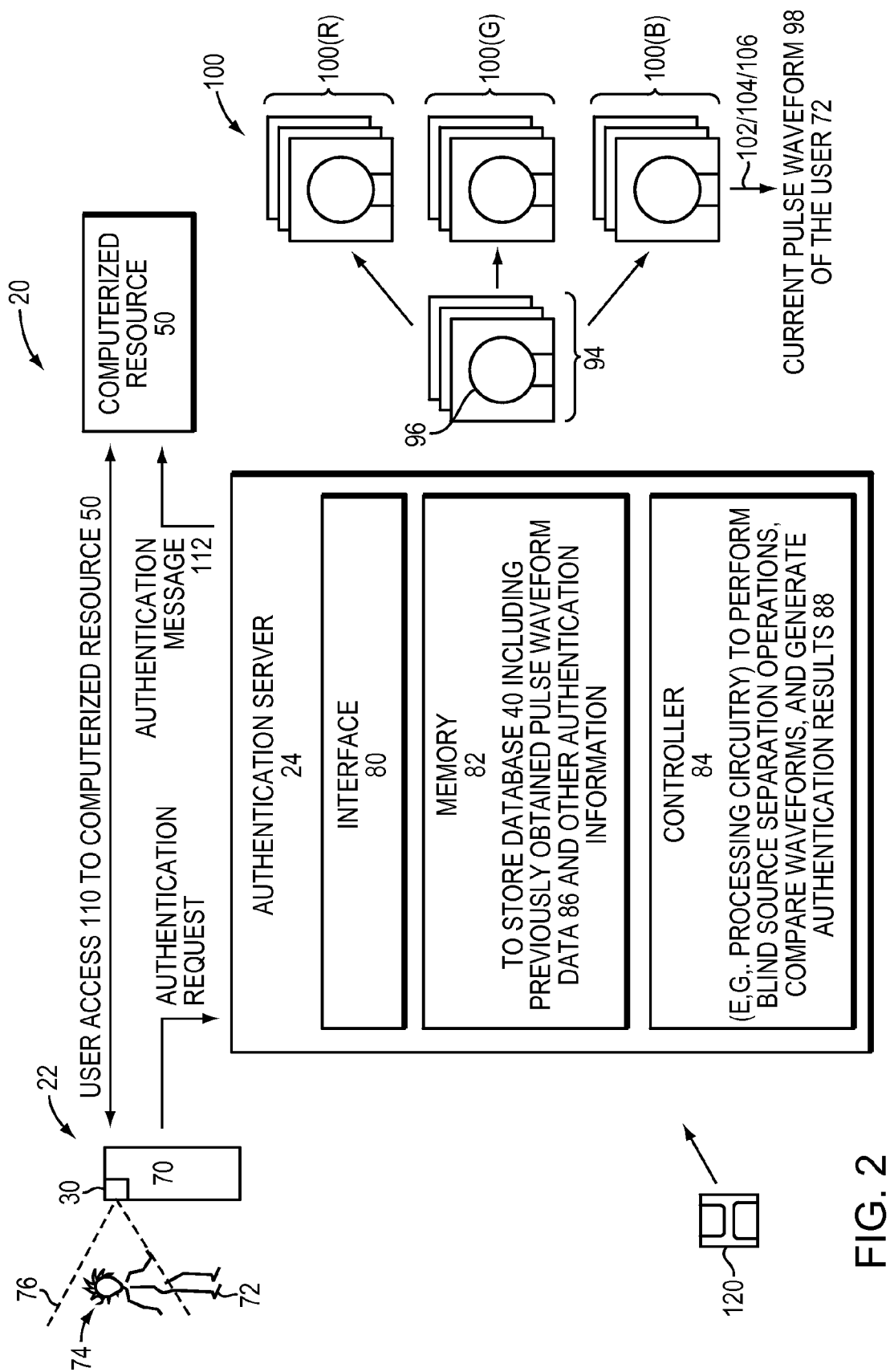
FIG. 2 is a block diagram of an example of the environment of FIG. 1 during an authentication process.

Referring to FIG. 2, there is illustrated an example of the environment of FIG. 1 during an authentication process. There is shown a user apparatus 22 including a camera 30 and processing circuitry 70 for assisting in the authentication of the user. When a user 72 operates the user apparatus 22 the user 72 positions their face 74 within a field of view 76 of the camera 30. The processing circuitry 70 then buffers and transmits captured video from the camera 30 (or alternatively performs certain local processing before transmitting processed data) to the authentication server 24. Such a transmission may take place over a network (e.g., see the communications medium 28 in FIG. 1).

As further shown in FIG. 2, the authentication server 24 includes an interface 80, memory 82 and a controller 84. The interface 80 allows the authentication server 24 to communicate with other components of the environment 20 through the communications medium 28 (see FIG. 1). In this embodiment, the memory 82 stores the database 40 comprising biometric data which includes previously obtained pulse waveform data 86 (e.g., representations of human pulse waveforms themselves, pulse waveform measurements, combinations thereof, etc.) as well as other data (e.g., user information). The controller 84 carries out authentication operations for initial authentication as well as continuous authentication during the access session by performing blind source separation operations to obtain current pulse waveforms, comparing the current pulse waveforms to expected pulse waveforms represented by the pulse data 86 stored in the database 40, and generating authentication results 88 to control access to the computerized resource 50.

Along these lines, suppose that the user 72 wishes to authenticate with the authentication server 24. It is assumed that the user has previously completed a setup process to store pulse waveform data 86 (i.e., representations of previous pulse waveforms) in the database 40 of the authentication server 24. To begin the authentication process, the user provides current video input 90 from the camera 30. In some embodiments, the user may also provide other user information to the authentication server 24. The user may communicate with the authentication server 24 directly as part of a front-end authentication process prior to attempting to access the computerized resource 50. Alternatively, the user may communicate with other circuitry to authenticate (e.g., the resource provider 26 in FIG. 1) and, in turn, that circuitry communicates with the authentication server 24 to initiate the authentication process. In either situation, the current video input 90 from the user apparatus 22 includes a series of video frames 94 which includes images of the user's face 96. The other user information may include a user identifier to indicate who the user claims to be and perhaps other authentication factors such a password or personal identification number (PIN), a one-time passcode (OTP), date and time information, specific software and hardware information, ISP information, other authentication factors, combinations thereof, and so on. As discussed above, biometric identification (e.g., based on the video input 90 of the user's face) avoids the need to enter user information. In such a scenario it will be appreciated that the current video input 90 from the user apparatus 22 may provide the user identifier.

Next, the authentication server 24 performs an authentication operation which considers a current pulse waveform 98 of the user 72. To obtain the current pulse waveform 98 of the user 72, the controller 84 performs a cardiac pulse recovery operation on the series of video frames 94. Along these lines, the controller 84 detects a region of interest (ROI) within the series of video frames 94 (e.g., using a standard face tracker). The controller 84 then decomposes the ROI into individual color channels 100 (e.g., a red color channel 100(R), a green color channel 100(G), and a blue color channel 100(B)) and spatially averages the ROI to obtain raw RGB traces 102. The controller 84 then applies Independent Component Analysis (ICA) 104 on the RGB traces 102 to recover multiple independent source signals 106. From the independent source signals 106, the controller 84 acquires the current pulse waveform 98 of the user 72. Additional information regarding such a process or a similar process and embellishments thereto can be found in an article entitled "Non-contact, automated cardiac pulse measurements using video imaging and blind source separation", written by Ming-Zher Poh, Daniel J. McDuff, and Rosalind W. Picard, and provided by Optics Express, Vol. 18, No. 10, May 10, 2010, the contents and teachings of which are hereby incorporated by reference in their entirety (hereinafter referred to as "the Poh reference").

It should be understood that this technique of obtaining the current pulse waveform 98 of the user 72 from the series of video frames 94 captured by the camera 30 of the user apparatus 22 is non-invasive to the user 72. In particular, there is no physical contact with the user required. Rather, the user 72 is physically separated from the camera 30 and simply moves his or her face 74 into the viewing field 76 of the camera 30. Moreover, there is no special hardware required. Rather, the technique simply leverages off of the existing video capture circuitry of the user apparatus 22.

Once the controller 84 of the authentication server 24 has obtained the current pulse waveform 98 of the user 72, the controller 84 compares the current pulse waveform 98 to an expected pulse waveform represented by pulse data 86 for the user 72. It should be understood that the effectiveness of this comparison is based on the individual identifying characteristics of one human pulse to another, thus enabling human pulse waveforms to operate as a means of identifying users among each other, e.g., as explained in the Shen reference.

To obtain the expected pulse waveform represented by the pulse data 86, the controller 84 retrieves the pulse data 86 for the user from the database 40 stored in the memory 82. In some arrangements, one or more entries are retrieved from the database 40 based on the user identifier. As will be explained shortly, the controller 84 is capable of making pulse waveform adjustments prior to performing the comparison (e.g., averaging particular waveform measurements from multiple entries of the pulse data 86, correcting based on circadian rhythms, compensating for aging since the pulse data 86 was taken, and so on).

Based on the comparison between the current pulse waveform 98 and the expected pulse waveform based on the pulse data 86 from the database 40, the controller 84 generates an authentication result 88 which is then used to control access 110 to the computerized resource 50. If the result 88 is deemed to be successful, the controller may establish an access session in which the user can access the computerized resource.

Additionally, in this exemplary embodiment, if authentication to the computerized resource is granted, the authentication operation is continuously repeated throughout the access session. In such continuous authentication, a similar process to that as described above is repeated. For example, the user of user apparatus 22 has their face captured by the camera 30 of the user apparatus 22 during the access session. The users face may be captured continuously during the access session by the camera delivering a constant stream of biometric data that can be used to continuously authenticate the user in real-time such that if the user were to leave the field of view of the camera, or a new user appeared in the field of view replacing the authorized user, the controller may deny access to the resource requiring the user to re-authenticate. The processing circuitry of the environment 20 may obtain current pulse data from the current video input of the user in real-time during the access period, perform a comparison between the current pulse data and expected pulse data and generate an authentication result based on the comparison between the current pulse data and the expected pulse data. The authentication result is used for authenticating the user during the access session. If the result is successful, the controller will continue to grant access to the resource. If the result is unsuccessful, the controller will deny access to the resource or challenge the user in order to ascertain if the user is the authenticated user. In this way, the user is subjected to a continuous authentication such that an unauthorized user may not simply replace the authorized user during the access session without being immediately authenticated. Additionally, as discussed above, if the authorized user leaves the resource the controller will simply cancel or revoke the authorization.

At this point, it should be understood that the controller 84 of the authentication server 24 is capable of being implemented in a variety of ways including via one or more processors running specialized software, application specific ICs (ASICs), field programmable gate arrays (FPGAs) and associated programs, discrete components, analog circuits, other hardware circuitry, combinations thereof, and so on. In the context of one or more processors running specialized software, a computer program product is capable of delivering all or portions of the software. The computer program product 120 has a non-transitory (or non-volatile) computer readable medium which stores a set of instructions which controls one or more operations controller 84. Examples of suitable computer readable storage media include tangible articles of manufacture and apparatus which store instructions in a non-volatile manner such as CD-ROM, flash memory, disk memory, tape memory, and the like.

Figure 3:
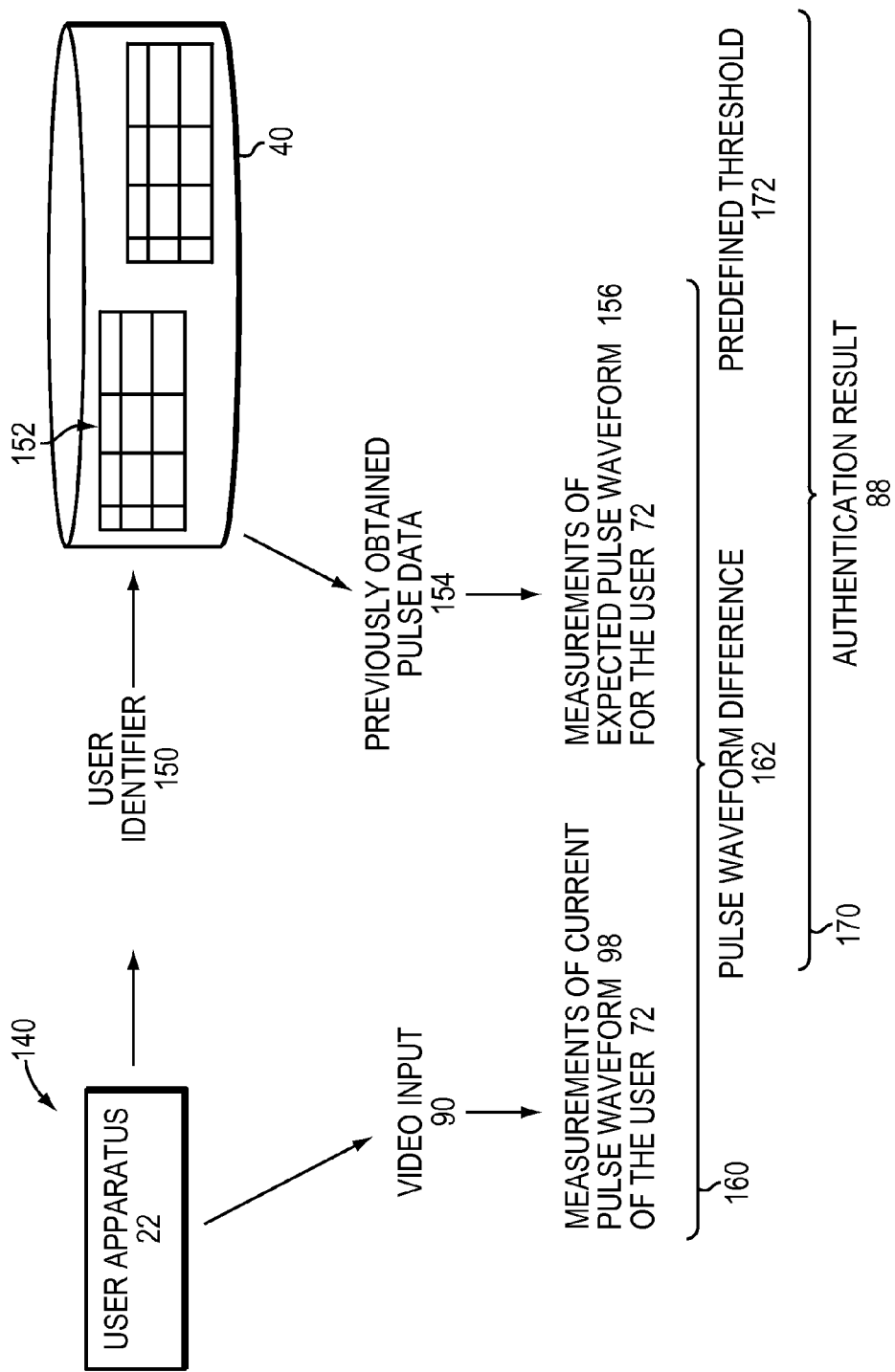
FIG. 3 is a block diagram of an example of a general authentication operation which is performed by control circuitry.
Figure 4:
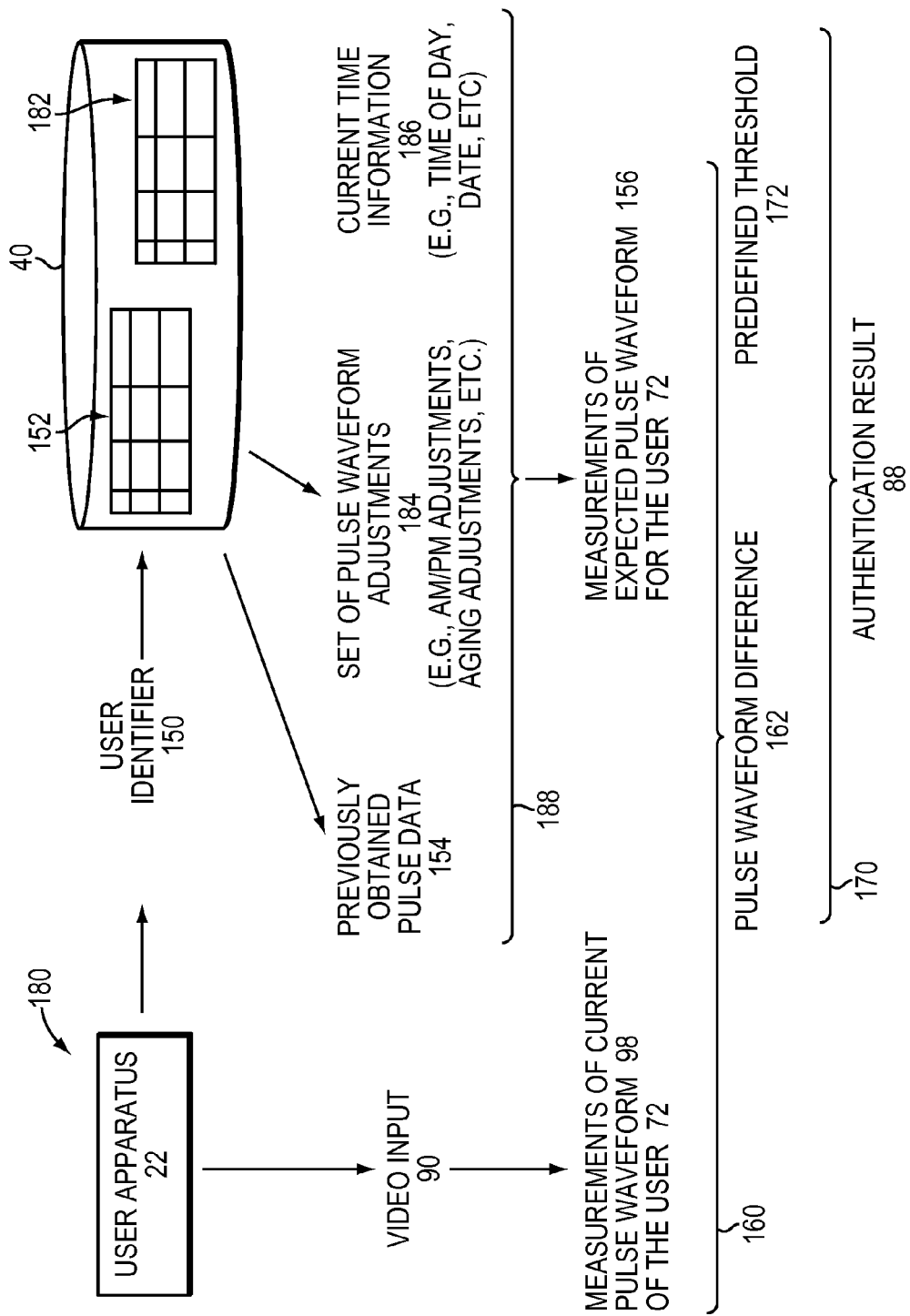
FIG. 4 is a block diagram of an example of an advanced authentication operation which is performed by control circuitry.

Referring to FIGS. 3 and 4, there is illustrated example authentication operations which are capable of being performed by the controller 84. In particular, FIG. 3 shows a general authentication operation 140 which is capable of being performed by the controller 84 of the authentication server 24. FIG. 4 is an advanced authentication operation 180 which is capable of being performed by the controller 84 of the authentication server 24.

As shown for the general authentication operation 140 in FIG. 3, the user apparatus 22 provides the video input 90 from which the controller 84 derives the measurements of the current pulse waveform 98 of the user 72. In some arrangements, the controller 84 performs video imaging and blind source separation operations on the video input 90 to obtain the measurements of the current pulse waveform 98 (e.g., also see FIG. 2 and the Poh reference).

Additionally, the user apparatus 22 further may provide other user information including a user identifier 150 which identifies the user 72 among multiple users 72. The controller 84 then accesses the entries 152 within the database 40, and retrieves previously obtained pulse data 154 of the user 72 (see also the pulse data 86 in FIG. 2). In some arrangements, each pulse data entry 152 includes a user identifier 150 to identify a user 72, pulse data 86 of that user 72, and timestamps to identify times of day and dates relating to the pulse waveform, among other things. For example, such timestamps may identify the date/time the waveform was collected, the date/time the waveform was stored, and/or the date/time the waveform was analyzed, among other things. From this collective information (i.e., the pulse data 154), the controller 84 generates a set of measurements for an expected cardiac pulse waveform 156 for the user 72. In some arrangements, the controller 84 combines previous waveform measurements to generate the expected cardiac pulse waveform 156.

As illustrated by the bracket 160, the controller 84 then computes a pulse waveform difference 162 from the measurements of the current pulse waveform 98 of the user 72 from the user apparatus 22 and the measurements of the expected pulse waveform 156 for the user 72 from the database 40. The pulse waveform difference 162 is an objective indicator of how closely the current pulse waveform 98 matches the expected pulse waveform 156 from a pattern matching perspective. That is, this pulse waveform difference 162 (e.g., a set of individual differences, an aggregation or summation of individual differences, a weighted score, etc.) serves as an indication of the likelihood that the current pulse waveform 98 is the legitimate user as identified by the user identifier 150. It will be appreciated that the larger the pulse waveform difference 162, the greater the likelihood that the user 72 is not legitimate.

It should be understood that, as is commonly the case with biometrics, the newly measured pulse characteristics may not exactly match previously measured pulse characteristics. Rather, some difference is to be expected when the legitimate user authenticates. Nevertheless, as in other forms of biometric authentication, successful match criteria requires the difference (in this case, the pulse waveform difference 162) to fall within a predefined threshold as explained further below.

As illustrated by the bracket 170, the controller 84 then compares the pulse waveform difference 162 to a predefined threshold (or set of thresholds) 172 to generate an authentication result 88. For example, in some arrangements, if the pulse waveform difference 162 is less than (or equal to) the predefined threshold 172, the controller 84 considers the user 72 to be legitimate and outputs, as the authentication result 88, a value indicating successful authentication. In these arrangements, if the pulse waveform difference 162 is greater than the predefined threshold 172, the controller 84 considers the user 72 to be an imposter and outputs, as the authentication result 88, a value indicating unsuccessful authentication based on pulse waveform.

In some arrangements, the predefined threshold 172 is initially set to a default setting at authentication server startup time. Later, an administrator of the authentication server 24 is able to change the default setting (e.g., lower the predefined threshold 172 to increase protection of the computerized resource 50, increase the predefined threshold 172 to lower protection of the computerized resource 50, etc.).

Additionally, it should be understood that the authentication result 88 is capable of directly controlling access to the computerized resource 50 (FIGS. 1 and 2). In particular, in some arrangements, the controller 84 grants access to the computerized resource 50 when the authentication result 88 has the successful authentication value, and denies access to the computerized resource 50 when the authentication result 88 has the unsuccessful authentication value.

As shown in FIG. 4, the controller 84 is capable of performing an advanced authentication operation 180 rather than the general authentication operation 140 of FIG. 3. The advanced authentication operation 180 is similar to the general authentication operation 140, but the advanced authentication operation 180 is capable of accommodating subtle changes in human pulse waveforms over time (e.g., based on time of day, based on aging, etc.).

Along these lines, the database 40 is capable of storing enhanced human pulse waveform information 182 which enables the controller 84 to derive a set of pulse waveform adjustments 184. Such a set of pulse waveform adjustment 184 enables the controller 84 of the authentication server 24 to factor in current time information 186 (e.g., time of day, amount of time elapsed since last authentication date, etc.) and identify replay video attacks such as an imposter trying to replay a video of the legitimate user taken in the morning during authentication operations in the evening, or a video of the legitimate user taken several years ago.

Such a set of pulse waveform adjustments 184 may include user-specific adjustments for the time of day (e.g., circadian rhythm parameters). For example, suppose that the controller 84 has collected enough previous pulse waveform data in the database 40 from the legitimate user that the controller 84 has determined that the legitimate user's pulse waveform is slightly different in shape in the evening (e.g., due to improved cardiac efficiency later in the day). To compensate for this circadian-style change in pulse waveform during the day, the controller 84 is capable of performing an adjustment operation 188 (shown by the bracket 188) to generate the measurements of the expected pulse waveform 156 for the user 72. The adjustment operation 188 may involve increasing (or decreasing) one particular measurement or multiple measurements. For instance, the controller 84 can adjust a nominal expected pulse waveform 156 by a morning-side set of adjustment factors for authentication operations in the morning (A.M.), and by an evening-side set of adjustment factors for authentication operations in the evening (P.M.).

Alternatively, the adjustment operation 188 may involve ignoring certain previously obtained measurements of cardiac pulse waveforms obtained from the user during times of days that were outside a particular time of day (e.g., querying the database 40 for only evening user pulse data 86 if authentication is performed during the evening, etc.). Since people have different biorhythms, such operation enables the authentication server 24 to improve its ability to identify legitimate users as well as imposters.

As another example, suppose that the controller 84 has collected previous pulse data 86 in the database 40 from the legitimate user, but that the previous pulse data 86 was acquired several years ago. In some arrangements, the controller 84 is configured to make wave form adjustments 184 which predict a specific change (e.g., pregnancy, recovery from an injury, aging, etc.). Along these lines, suppose that the database 40 includes the user's age (e.g., see the enhanced human pulse waveform information 182) and has determined that the user's pulse waveform should have changed in a particular manner (e.g., due to age, due to a unique heart condition or recovery from the condition, etc.). In these situations, the controller 84 is capable of compensating for this age-style change in the pulse waveform since the previous pulse waveform data was acquired. Again, the bracket 188 represents an adjustment operation 188, i.e., increasing or decreasing one or more measurements for an expected cardiac pulse waveform to accommodate for the elapsed time since the earlier pulse waveform data was obtained.

In other arrangements, the controller 84 is configured to adjust the predefined threshold 172 to factor in decay after such a long period of time. For example, if the current pulse data is a precise match or too close to the previous pulse data 86 acquired several years ago, the controller 84 may deem this to be a replay attack.

In yet other arrangements, the controller 84 is configured to trigger acquisition of new reference data. That is, due to the large amount of time that has passed, the controller 84 invalidates the previous pulse data 86 acquired several years ago and collects new data for future authentication.

It should be understood that other modifications can be made as well. For example, geo-location may be factored into the adjustments. In particular, if the setting is a doctor's office or an exercise facility, adjustments may be made to slightly modify the expected pulse waveform in a particular manner or broaden the acceptable uncertainty. due to anxiety, exercise, caffeine, and so on. Alternatively, if the setting is a passive location, adjustments may be made to slightly modify the expected pulse waveform in an opposite manner. Such adjustments are purposeful in order to detect replay attacks from imposters.

Figure 5:
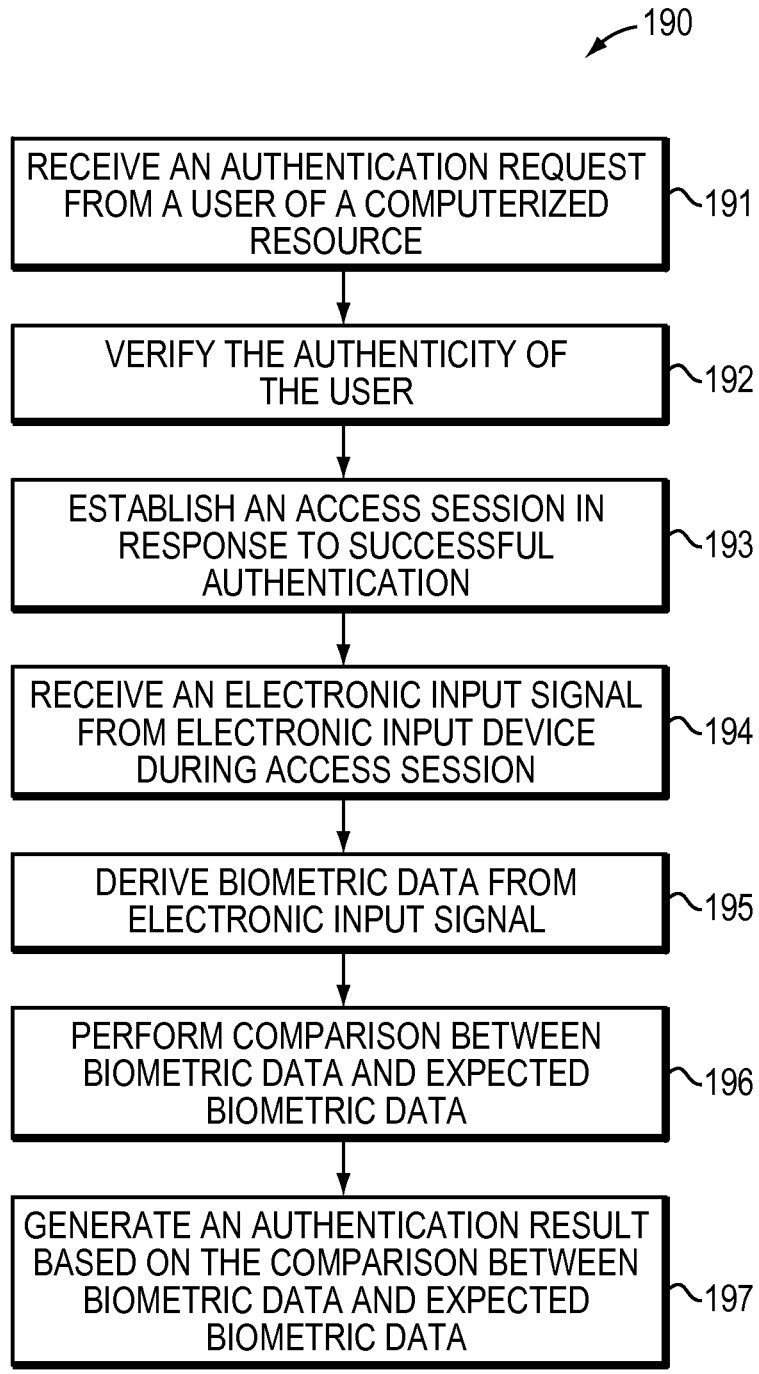
FIG. 5 is a flowchart of a procedure which is performed by circuitry of the environment of FIG. 1 when performing authentication operations.

Referring to FIG. 5, there is illustrated a flowchart of a procedure 190 which is performed by the controller 84 of the authentication server 24 when performing authentication operations. In step 191, the controller 84 receives an authentication request from a user of a computerized resource. The request comprises a user identifier identifying the user. The authentication request may involve transmitting a user identifier such as a username and/or password. It should also be understood that the authentication request may involve transmitting biometric identification so that the biometric identification acts as the user identifier. In this arrangement, the biometric identification avoids the need to enter a username and/or password. In step 192, the controller 84 verifies the authenticity of the user based on the user identifier identifying the user. In step 193, the controller 84 establishes an access session in which the user can access the computerized resource in response to successfully verifying the authenticity of the user. In step 194, the controller receives an electronic input signal from an electronic input device during the access session. The electronic input device is configured to take a biometric measurement from the user. In step 195, the controller derives biometric data from the electronic input signal. For example, the biometric data may be the current cardiac pulse data. In step 196, the controller performs a comparison between the biometric data from the user and expected biometric data for the user. The expected biometric data may be stored in the database 40 and include previously obtained cardiac pulse data for the user. In step 197, the controller 84 generates an authentication result based on the comparison between the biometric data and the expected biometric data. For example, the authentication result may be based on the comparison between the cardiac pulse data and the expected cardiac pulse data. The authentication result can be used for further authentication of the user during the access session. The authentication process as described in steps 194 to 197, inclusive, may be repeated continuously throughout the access session.

Figure 6:
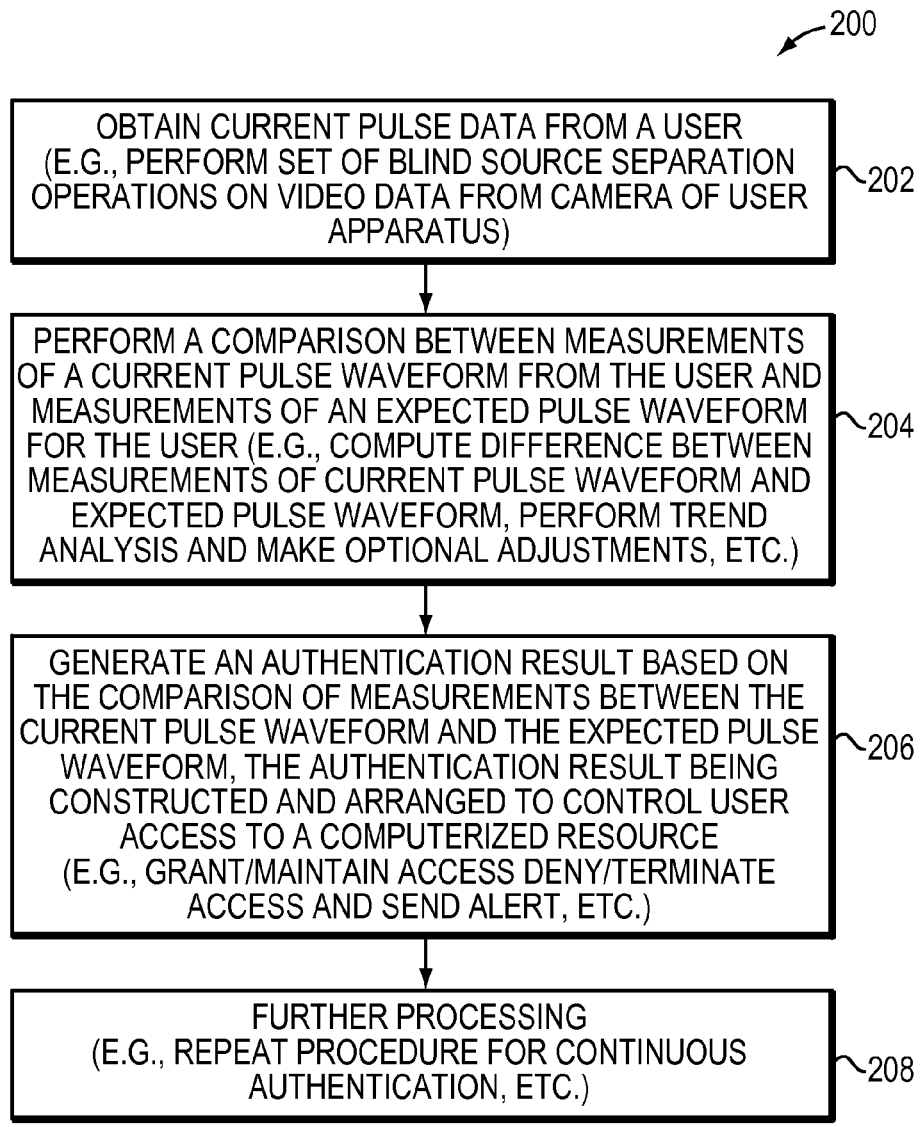
FIG. 6 is a flowchart of a procedure which is performed by circuitry of the environment of FIG. 1 when performing authentication operations using pulse data.

Referring to FIG. 6, there is illustrated a flowchart of a procedure 200 which is performed by the controller 84 of the authentication server 24 when performing authentication operations using pulse data. In step 202, the controller 84 obtains current pulse data from a user 72 of a user apparatus 22 (also see FIG. 1). The user 72 may wish to authenticate in order to remotely access a computerized resource 50 on a resource provider 26 such as a remote server or online store. Alternatively, the computerized resource 50 may reside locally on the user apparatus 22 (e.g., the user attempting to login or unlock a computer, tablet or smart phone).

In step 204, the controller 84 performs a comparison between the current pulse data from the user and expected pulse data for the user. In some arrangements, the controller 84 derives measurements of a current pulse waveform 98 of the user 72 based on video input 90 from a camera 30 of the user apparatus 22 in a non-contact manner (also see FIG. 2). Along these lines, the controller 84 performs a set of blind source separation operations and ICA on the video input 90 which captures the user's face 74.

Additionally, the controller 84 obtains measurements of an expected cardiac pulse waveform 156 for the user 72 based on previously obtained pulse data 86 of the user 72 which is stored in entries 152 of the database 40 (FIG. 3). In some arrangements, the controller 84 adjusts the measurements of the expected cardiac pulse waveform 156 based on a set of pulse waveform adjustments 184 such as circadian rhythms to factor in changes in pulse waveforms during a 24-hour window, and aging trends to factor in changes in pulse waveforms over an extended amount of time (e.g., years).

In step 206, the controller 84 generates an authentication result 88 based on the comparison between the current pulse data and the expected pulse data. In particular, the controller 84 computes differences in measurements of a current pulse waveform 98 of the user 72 and an expected pulse waveform 156 for the user 72. The authentication result 88 is constructed and arranged to control user access to the computerized resource 50.

In step 208, the controller 84 performs further processing. In this embodiment, if authentication is successful, the controller 84 performs authentication in a continuous manner during the access session. For example, the user 72 may be participating in an online meeting and thus provide a continuous video stream as the video input 90 for continuous authentication throughout the access session. In these arrangements, step 208 proceeds back to step 202 to repeat the procedure 200.

In step 208, if authentication is successful, the controller 84 may update the database 40 to include the current pulse data within a new entry 152, maintain access if the user 72 had previously successfully authenticated during a continuous authentication session, and so on. However, if authentication is unsuccessful, the controller 84 may perform a remedial action such as send an alert to an administrator of the environment 20, deny access to the computerized resource 50, terminate access if the user 72 had previously successfully authenticated during a continuous authentication session, provide a different challenge to the user 72, and so on.

As described above, improved techniques are directed to performing authentication operations which use pulse data from a user 72. Since such techniques require the presence of a human pulse, a perpetrator cannot simply submit a photograph of a legitimate user's face to circumvent the authentication process. Rather, the photograph would provide no pulse and thus fail authentication. In some arrangements, the improved techniques involve the capture of videos of human faces and derivation of user-distinctive cardiac pulse waveforms from the videos (i.e., human pulse waveforms used for identification). For such arrangements, standard webcams can be used to capture the videos. Moreover, such techniques are capable of factoring in pulse waveform trends such as changes in pulse waveform during the day (e.g., circadian rhythm adjustments) and changes in pulse waveform over years (e.g., aging adjustments) to detect and thwart video replay attacks.

Figure 7:
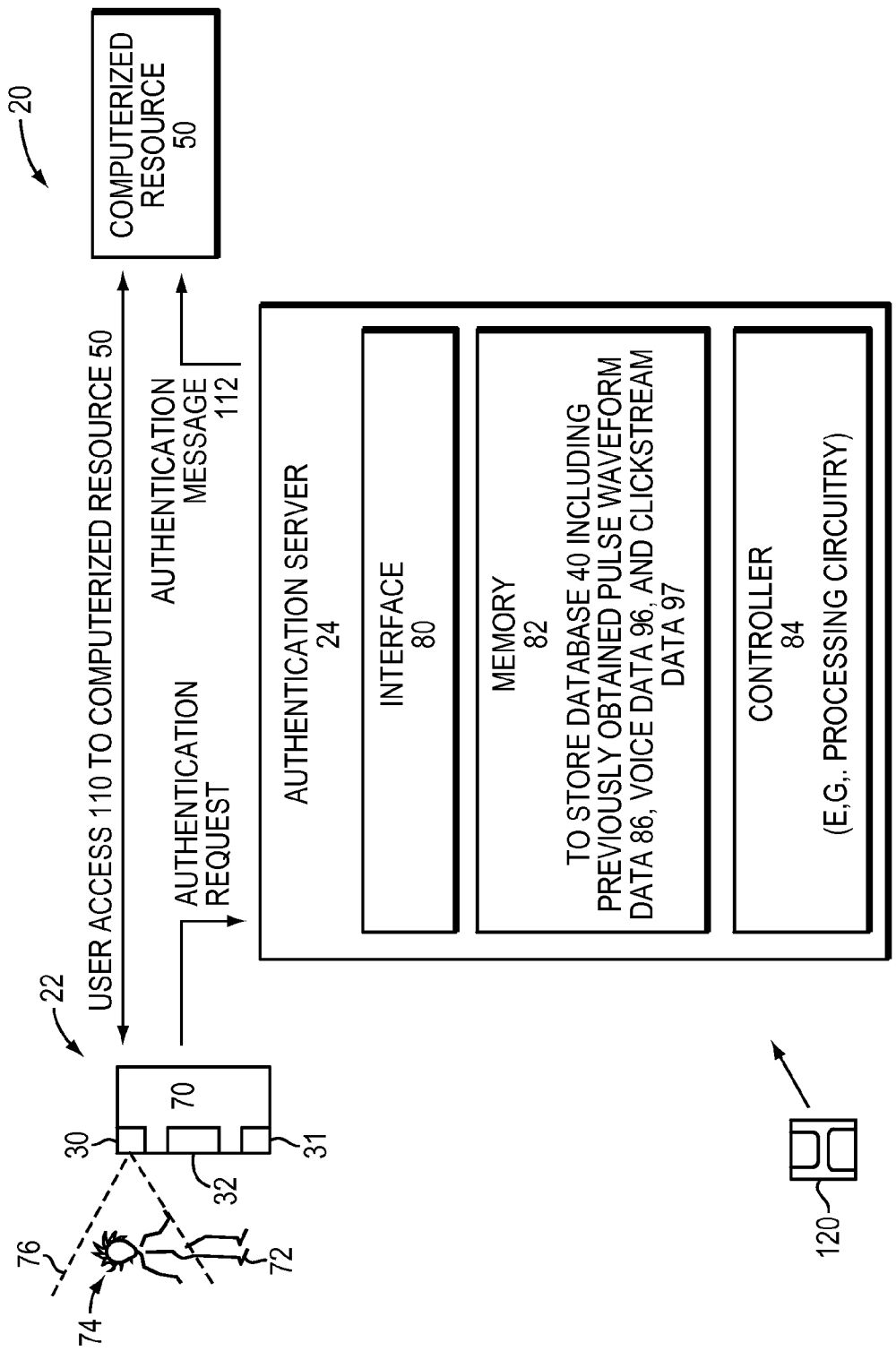
FIG. 7 is a block diagram of another example of the environment of FIG. 1 during an authentication process.

Referring to FIG. 7, there is illustrated another example of the environment of FIG. 1 during an authentication process. In this embodiment, the authentication server 24 includes a database 40 which includes biometric data relating to pulse waveform 86, voice 96 and clickstream 97. It will be known in the art that individuals have distinct click rates that enable the identity of an individual to be identified by clickstream analytics. The database 40 may contain such data enabling identification of the individual. The database contains voice data enabling voice recognition. The database may also contain other user authentication information as well. The user apparatus 22 includes a camera 30, a microphone 31, a keyboard 32 which act as multiple biometric input devices such that these devices can send constant streams of video data, voice data and clickstream data that can be used to authenticate the user.

The authentication operation described herein is substantially similar to those operations as described with respect to previous figures. The controller 84 receives the authentication request from the user. The request comprises a user identifier. The identifier may be a username, biometric identification or the like. The controller 84 verifies the user based on the identifier and establishes an access session in response to successful verification of the user. If the user identifier is a biometric identification, the controller will compare, for example, the current pulse data derived from the video of users face with expected pulse data in the database. This has been described in detail with respect to previous figures. However, in this embodiment, the biometric identification may also be a voice in which case the controller would compare the voice captured by the microphone with the voice data in the database. The controller would establish a user session in response to successful verification.

Once the access session has been established, the controller 84 receives an electronic input signal from an electronic input device during the access session. The electronic input device may be a camera, a microphone or a keyboard to take a biometric measurement from the user. In this particular embodiment, the controller receives a continuous input signal from the keyboard and derives from the signal data such that the controller can determine the intervals between characters inserted through the keyboard and the overall speed, rhythm and pattern of the input. The controller can compare the data with the clickstream data in the database 40 to verify the user. If the comparison is successful the user may continue to access the computerized resource as per normal. However, if the comparison is unsuccessful, the controller 84 may request video from the camera or a voice from the microphone to authenticate the user during the access session. It will be appreciated that the camera and the microphone may be in an inoperative mode until the unsuccessful comparison of current input data and clickstream data in the database. For example, when access is granted and the current keyboard input data is continuous during browsing and writing documents in the computerized resource the video and microphone are not required. When detecting absence of feeds from keyboard or a change in pattern, the controller may require video of the users face from the camera for verification of the user. The controller will derive current pulse data from the video, compare with expected data in database and generate authentication result as described above with respect to the other figures. If the verification or authentication is successful, the session continues as per normal. If the verification or authentication is unsuccessful, for example, the user has left the field of view of the camera, the controller will request a voice or sound from microphone for verification. If the voice or sound is also unsuccessful, the authentication of the user is revoked. If it is successful, for example, the user is outside the field of view but close to the computer to be heard by microphone, the authentication will be successful, and the access session will continue. The authentication of the user during the access session will also continue.

While various embodiments of the invention have been particularly shown and described, it will be understood by those skilled in the art that various changes in form and details may be made therein without departing from the spirit and scope of the invention as defined by the appended claims.

For example, the authentication process was described above as being primarily performed remotely within the authentication server 24 by way of example only. In other arrangements, the authentication process is performed elsewhere such as locally within a user apparatus 22 (e.g., for local login access), or at the resource provider 26 (e.g., when the resource provider maintains oversight/responsibility for authentication).

Additionally, it should be understood that the authentication result 88 may be combined with other security mechanisms. For example, the same video input 90 which is used to derive the current pulse waveform 98 of the user 72 includes other information such as facial geometries, facial features and facial component distances for processing by a facial recognition mechanism. Also, other artifacts (e.g., mouth movement, accompanying noise, lighting, background data, etc.) may be used as factors in combination with pulse waveform derivation for vitality detection, voice identification, location identification, and so on.

Furthermore, it should be understood that a variety of remedial activities are available in the event the authentication result 88 indicates unsuccessful authentication. For example, the controller 84 may terminate an existing user session, or deny access to the computerized resource. Alternatively, the controller 84 may issue challenges for other information, and so on.

Moreover, in some arrangements, the database 40 (e.g., see FIGS. 3 and 4) is part of a larger authentication database such as a multi-factor authentication database, or a risk-based or adaptive authentication database. In other arrangements, the database 40 is maintained separately and independently.

Additionally, it should be understood that the above-described video input processing technique is one particular way of obtaining a pulse waveform from video input. However, other techniques can be used as well. Along these lines, decomposing a region of interest (ROI) into individual color channels, spatially averaging the ROI to obtain raw traces, and applying Independent Component Analysis (ICA) was provided by way of example as a way to recover multiple independent source signals. Additionally, blind source separation operations were described by way of example only as being suitable for use when separating the current pulse waveform from other signals, artifacts, noise, etc. mixed within the video input. It should be understood that other computational operations may be suitable for use as well to obtain the pulse waveform from the video input.

Furthermore, it should be understood that the human face was described as the particular body part from which to obtain pulse waveforms. Since the human face may be captured for other purposes (e.g., liveliness testing, facial recognition, etc.), the same data is conveniently available for pulse waveform extraction. However, in other arrangements, a different body part is analyzed for pulse waveform extraction. For example, areas such as the wrist, neck, and so on, are parts of the body that express pulse in readily visible form. Additionally, while devices such as fingerprint scanners and eye scanners obtain images of other body parts for other forms of authentication (e.g., fingerprint recognition and retina recognition), such scanners can be used as a vehicle to obtain pulse data concurrently.

What is claimed is:

1. A method for use in authentication, comprising:
   performing a first authentication operation in connection with a user;
   based on the first authentication operation, generating an authentication result, the authentication result being constructed and arranged to control user access to a computerized resource;
   after the user has accessed the computerized resource in response to the authentication result indicating successful user authentication, performing a second authentication operation based on a first biometric;
   based on the second authentication operation, generating a new authentication result;
   wherein generating the new authentication result includes:
   in response to the new authentication result indicating successful user authentication, providing the user with continued access to the computerized resource, and
   in response to the new authentication result indicating unsuccessful user authentication, requesting input of a second biometric different to the first biometric in order to facilitate continued user access to the computerized resource.

2. The method as claimed in claim 1, wherein generating the new authentication result comprises outputting, as an authentication signal, a risk score based on at least one risk factor, wherein the result of the comparison between first biometric and expected biometric data is one risk factor.

3. The method as claimed in claim 2, further comprising:
   granting access to the computerized resource when the risk score is within a predefined threshold of certainty.

4. The method as claimed in claim 2, further comprising:
   denying access to the computerized resource when the risk score is outside a predefined threshold of certainty.

5. The method as claimed in claim 1, wherein biometric data is received during user access to the computerized resource.

6. The method as claimed in claim 5, wherein the biometric data is video data.

7. The method as claimed in claim 6, wherein the video data is of the user's face.

8. The method as claimed in claim 7, wherein performing the second authentication operation comprises performing a set of computational operations on the video data to identify, as at least part of the biometric data, a current cardiac pulse waveform of the user from the user's face.

9. The method as claimed in claim 8, wherein performing the second authentication operation comprises computing measurements of an expected cardiac pulse waveform for the user based on previously obtained biometric data for the user and comparing the current pulse waveform and the expected pulse waveform.

10. An electronic apparatus for use in authentication, comprising:
    an interface;
    a memory; and
    a controller coupled to the interface and the memory, the controller being constructed and arranged to:
    perform a first authentication operation in connection with a user;
    based on the first authentication operation, generate an authentication result, the authentication result being constructed and arranged to control user access to a computerized resource;
    after the user has accessed the computerized resource in response to the authentication result indicating successful user authentication, perform a second authentication operation based on a first biometric;
    based on the second authentication operation, generate a new authentication result;
    wherein the controller, when generating the new authentication result, is constructed and arranged to:
    in response to the new authentication result indicating successful user authentication, provide the user with continued access to the computerized resource, and
    in response to the new authentication result indicating unsuccessful user authentication, request input of a second biometric different to the first biometric in order to facilitate continued user access to the computerized resource.

11. The electronic apparatus as claimed in claim 10, wherein
    generating the new authentication result comprises outputting, as an authentication signal, a risk score based on at least one risk factor, wherein the result of the comparison between first biometric and expected biometric data is one risk factor.

12. The electronic apparatus as claimed in claim 11, wherein the controller is constructed and arranged to:
    grant access to the computerized resource when the risk score is within a predefined threshold of certainty.

13. The electronic apparatus as claimed in claim 11, wherein the controller is constructed and arranged to:
    deny access to the computerized resource when the risk score is outside a predefined threshold of certainty.

14. A computer program product having a non-transitory computer readable medium which stores a set of instructions for use in authentication, the set of instructions causing a computer to perform a method of:
    performing a first authentication operation in connection with a user;
    based on the first authentication operation, generating an authentication result, the authentication result being constructed and arranged to control user access to a computerized resource;
    after the user has accessed the computerized resource in response to the authentication result indicating successful user authentication, performing a second authentication operation based on a first biometric;
    based on the second authentication operation, generating a new authentication result;
    wherein generating the new authentication result includes:
    in response to the new authentication result indicating successful user authentication, providing the user with continued access to the computerized resource, and in response to the new authentication result indicating unsuccessful user authentication, requesting input of a second biometric different to the first biometric in order to facilitate continued user access to the computerized resource.

15. The computer program product as claimed in claim 14, wherein generating the new authentication result comprises outputting, as an authentication signal, a risk score based on at least one risk factor, wherein the result of the comparison between first biometric and expected biometric data is one risk factor.

16. The computer program product as claimed in claim 15, wherein the set of instructions causing a computer to perform a further step of:

granting access to the computerized resource when the risk score is within a predefined threshold of certainty.

17. The computer program product as claimed in claim 15, wherein the set of instructions causing a computer to perform a further step of:

denying access to the computerized resource when the risk score is outside a predefined threshold of certainty.

\* \* \* \* \*